United States Patent [19]
Roach et al.

[11] Patent Number: 5,413,568
[45] Date of Patent: May 9, 1995

[54] REFASTENABLE ADHESIVE FASTENING SYSTEMS FOR INDIVIDUALLY PACKAGED DISPOSABLE ABSORBENT ARTICLES

[75] Inventors: Jennifer A. Roach; Douglas Toms, both of Cincinnati; Ted L. Blaney, West Chester; M. Elizabeth P. Chisholm, Cincinnati, all of Ohio

[73] Assignee: The Procter & Gamble Company, Cincinnati, Ohio

[21] Appl. No.: 194,817

[22] Filed: Feb. 14, 1994

Related U.S. Application Data

[63] Continuation of Ser. No. 934,147, Aug. 21, 1992, abandoned.

[51] Int. Cl.⁶ ..................... A61F 13/15; A61F 13/20
[52] U.S. Cl. ................... 604/358; 604/385.1; 604/389; 604/390; 604/393; 206/440
[58] Field of Search ............ 206/440; 602/57; 604/358, 385.1, 386, 389, 390, 393

[56] References Cited

U.S. PATENT DOCUMENTS

| | | |
|---|---|---|
| 3,089,494 | 5/1963 | Schwartz . |
| 3,604,423 | 9/1971 | Fraser . |
| 3,630,201 | 12/1971 | Endres . |
| 3,646,937 | 3/1972 | Gellert . |
| 3,848,594 | 11/1974 | Buell . |
| 3,853,129 | 12/1974 | Kozak . |
| 3,867,940 | 2/1975 | Mesek et al. . |
| 3,921,638 | 11/1975 | Schaar . |
| 3,971,380 | 7/1976 | Tritsch . |
| 3,973,567 | 8/1976 | Srinivasan et al. . |
| 4,010,753 | 3/1977 | Tritsch . |
| 4,025,373 | 5/1977 | Hirsch et al. . |
| 4,182,333 | 1/1980 | Schaar . |
| 4,210,144 | 7/1980 | Sarge, III et al. . |
| 4,237,889 | 12/1980 | Gobran . |
| 4,248,918 | 2/1981 | Hornibrook et al. . |
| 4,292,360 | 9/1981 | Riedel et al. . |
| 4,317,449 | 3/1982 | Nowakoski . |
| 4,318,408 | 3/1982 | Korpman . |
| 4,342,815 | 8/1982 | Doehnert . |
| 4,376,147 | 3/1983 | Byrne et al. . |
| 4,377,159 | 3/1983 | Hansen . |
| 4,436,520 | 3/1984 | Lipko et al. . |
| 4,540,415 | 9/1985 | Korpman . |
| 4,556,146 | 12/1985 | Swanson et al. . |
| 4,608,047 | 8/1986 | Mattingly . |
| 4,655,761 | 4/1987 | Grube et al. . |

(List continued on next page.)

FOREIGN PATENT DOCUMENTS

| | | |
|---|---|---|
| 0316601A2 | 5/1989 | European Pat. Off. . |
| 0336639A2 | 10/1989 | European Pat. Off. . |
| 0357000 | 3/1990 | European Pat. Off. ............ 604/358 |
| 0418951A2 | 3/1991 | European Pat. Off. . |
| 1597799 | 9/1981 | United Kingdom . |
| WO89/02729 | 9/1987 | WIPO . |
| WO88/07336 | 10/1988 | WIPO . |
| WO89/02728 | 4/1989 | WIPO . |
| 8902728 | 4/1989 | WIPO ................ 604/358 |

*Primary Examiner*—Randall L. Green
*Assistant Examiner*—P. Zuttarelli
*Attorney, Agent, or Firm*—Jeffrey V. Bamber; Steven W. Miller; E. Kelly Linman

[57] ABSTRACT

An individual absorbent article package, such as a sanitary napkin wrapper and an adhesive fastening system for such a wrapper are disclosed. The adhesive fastening system comprises a tape tab having an adhesive for releasably securing the wrapper and sanitary napkin in a folded configuration prior to and after use. The adhesive is adhered to a landing surface such as a portion of the sanitary napkin wrapper that forms part of the package body. The landing surface need not be reinforced to prevent tearing upon opening of the package. The fastening system provides bond security while at the same time making the fastening system easy to open without tearing by carefully matching of the properties of the adhesive, the tape tab, and the landing surface. The surface characteristics, elasticity modulus, and caliper of the landing surface are specified. The agressiveness (quick-stick) and coating weights of the adhesive are carefully selected to provide an adhesive fastening system that bonds easily, holds securely and is refastenable.

10 Claims, 3 Drawing Sheets

U.S. PATENT DOCUMENTS

| | | | |
|---|---|---|---|
| 4,704,115 | 11/1987 | Buell . | |
| 4,710,190 | 12/1987 | Wood et al. . | |
| 4,728,325 | 3/1988 | Spiller . | |
| 4,743,242 | 5/1988 | Grube et al. . | |
| 4,753,649 | 6/1988 | Pazdernik . | |
| 4,762,888 | 8/1988 | Sun et al. . | |
| 4,769,283 | 9/1988 | Sipinen et al. . | |
| 4,869,724 | 9/1989 | Scripps . | |
| 4,880,422 | 11/1989 | McBride . | |
| 4,894,060 | 1/1990 | Nestegard . | |
| 4,917,675 | 4/1990 | Taylor et al. . | |
| 4,964,859 | 10/1990 | Feldman | 206/440 |
| 4,968,311 | 11/1990 | Chickering et al. | 604/385.1 |
| 4,973,326 | 11/1990 | Wood et al. . | |
| 4,983,174 | 1/1991 | Noreen et al. . | |
| 4,985,025 | 1/1991 | Lingertat et al. . | |
| 5,019,071 | 5/1991 | Bany et al. . | |
| 5,019,072 | 5/1991 | Polski . | |
| 5,024,672 | 6/1991 | Widlund . | |
| 5,026,446 | 6/1991 | Johnston et al. . | |
| 5,032,120 | 7/1991 | Freeland et al. . | |
| 5,061,262 | 10/1991 | Chen et al. . | |
| 5,066,289 | 11/1991 | Polski . | |
| 5,084,039 | 1/1992 | Cancio et al. . | |
| 5,106,383 | 4/1992 | Mulder et al. . | |
| 5,147,346 | 9/1992 | Cancio et al. . | |
| 5,147,347 | 9/1992 | Huang et al. . | |
| 5,342,339 | 8/1994 | Carpenter et al. | 604/389 |

U.S. Patent    May 9, 1995    Sheet 1 of 3    5,413,568
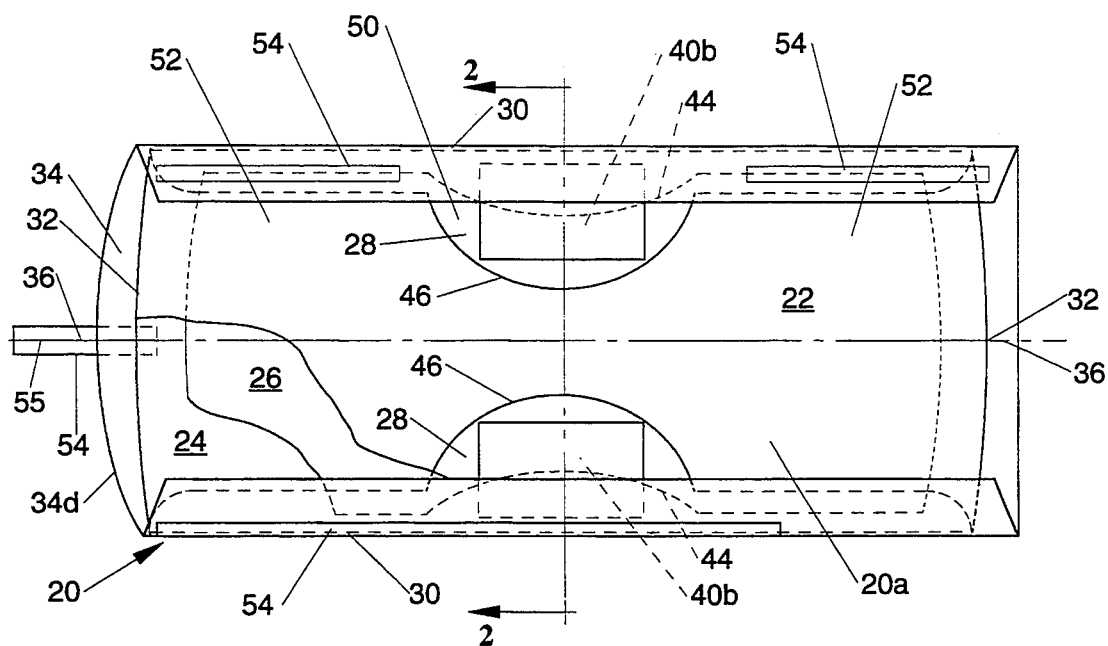
Fig. 1
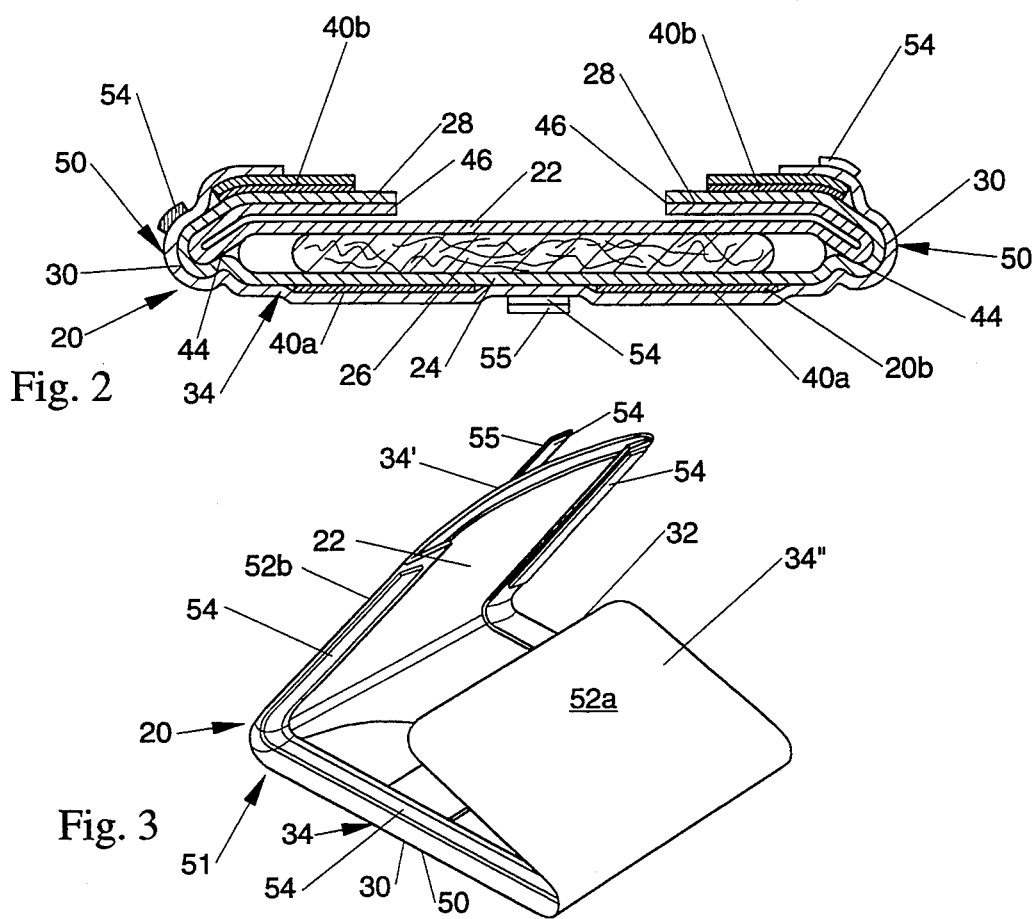
Fig. 2
Fig. 3

REFASTENABLE ADHESIVE FASTENING SYSTEMS FOR INDIVIDUALLY PACKAGED DISPOSABLE ABSORBENT ARTICLES

This is a continuation of application Ser. No. 07/934,147, filed on Aug. 21, 1992 now abandoned.

FIELD OF THE INVENTION

The present invention relates to adhesive fastening systems for packages for individually packaged disposable absorbent articles like sanitary napkins and adult incontinent products, and, more particularly, to a refastenable adhesive fastening system that bonds easily, holds securely, and is easily opened and refastened without tearing the package even if the package consists of a low caliper polyethylene film having no reinforcement for strength against tearing.

BACKGROUND OF THE INVENTION

Sanitary napkins used to collect vaginal discharges and adult incontinent products are well known in the art. Various arrangements for individually packaging such absorbent articles are also known in the art.

Individually packaged sanitary napkins are disclosed in U.S. Pat. No. 3,973,567 issued to Srinivasan, et al. on Aug. 10, 1976; U.S. Pat. No. 4,917,675 issued to Taylor, et al. on Apr. 17, 1990, European Patent Application Publication No. 0357000 A1 published in the name of Umesh on Mar. 7, 1990, and in U.S. Pat. No. 4,556,146 issued Dec. 3, 1985, to Swanson et al. The Swanson, et al. patent discloses a trifolded wrapper which packages a sanitary napkin, covers adhesive on the outwardly oriented face of the backsheet, and may be used for disposing of the used sanitary napkin.

Other trifolded arrangements are known, such as that disclosed in U.S. Pat. No. 3,604,423 issued Sep. 14, 1971 to Fraser and in International Publication WO 89/02728 published Apr. 6, 1989 in the name of Froidh et al. Discarding used sanitary napkins enveloped in the packaging is also taught in the art. For example, International Publication WO 89/02729 published Apr. 6, 1989 in the name of Pigneul and U.S. Pat. No. 4,608,047 issued Aug. 26, 1986 to Mattingly disclose two packaging arrangements intended for this purpose.

The search for improved individual packages for disposable absorbent articles such as sanitary napkins has, however, continued. In particular, the search for a refastenable fastening system for such packages which satisfies all the desired criteria for such packages, has continued.

For instance, the design of adhesive fastening systems for individual disposable absorbent article packages concentrates on two major criteria which are generally opposed to each other: adhesive bond security and refastenability. It is the goal of such adhesive fastening systems to achieve both strong adhesive bond security (a bond which remains adhered to the package until it is desired to open the package to remove the absorbent article), and non-destructive removal of the tape upon opening the package for refastenability of the fastener when disposing of the absorbent article within the package after use.

It has generally been believed that the peel force of a pressure-sensitive adhesive tape from a substrate is one of the most important factors in determining how an adhesive fastening system actually performs during use. The peel force property shows that higher peel forces improve the bond security of the fastening system while also making it more difficult to remove without tearing the article to which the adhesive is fastened (that is, the landing surface or landing member). Thus, early solutions to providing an improved adhesive fastening system focused on balancing the peel force in order to optimize bond security and refastenability. One focus area was on adjusting the properties of the elements of the adhesive fastening system. Particularly, the tensile strength (tear resistance) of the landing surface, typically the unreinforced packaging material, was increased so that the packaging material could withstand high tensile stresses caused by the tape removal. However, such package materials tended to be rigid, noisy, expensive and more burdensome on material resources and the environment (require more materials). In other attempts, the tape properties were adjusted to increase contact area and lower peel force so as to not exceed the strength of the package material. These systems were expensive, inconvenient and had low bond security at low application pressure.

As the demand was made for high bond security adhesive fastening systems to meet the conditions placed upon the package of individual packaged absorbent articles, additional strength had to be added to the package material to avoid tearing the same. This additional strength was added to the package material by increasing its thickness, and/or by reinforcing it such as by laminating additional materials to the inside or outside of the package material in the fastening area.

Accordingly, it is an object of this invention to provide a refastenable fastening system for the package of an individually packaged absorbent article, such as a sanitary napkin. It is further an object of this invention to provide an individually packaged sanitary napkin which is easy for the user to open. It is also an object of this invention to provide an individually packaged sanitary napkin having packaging which may be used for disposal of a used product. Finally, it is an object of this invention to provide improved closure mechanisms for maintaining the package in a closed configuration for disposal.

BRIEF SUMMARY OF THE INVENTION

The present invention comprises an individually packaged absorbent article comprising:
  an absorbent article having a body-facing side, a garment-facing side, two longitudinal and two lateral side margins, said absorbent article having an adhesive patch on said garment-facing side;
  a releasable wrapper releasably affixed to the adhesive patch on said garment-facing side, said wrapper being folded about at least two transverse axes to define a package body and a package flap; and
  an adhesive tape fastening system for fastening said package flap to said package body, said tape fastening system comprising:
   a) a tape tab comprising a first portion affixed to said package flap, and a second portion for releasably fastening to said package body, said tape tab comprising a fastening surface having an adhesive thereon; and
   b) a portion of said package body comprising a landing surface to which said fastening surface of said tape is adhered, said portion of said package body comprising a film having a nominal average caliper of between about 0.020 mm and about 0.036 mm, and wherein said tape fastening system has a Dynamic Shear Strength of greater than about 900 grams per centimeter.

The tape fastening system of the present invention is unique in that a single adhesive can be used to both securely attach (i.e., essentially permanently attach) the first portion to the package flap, and to releasably attach the second portion to a landing surface on the package body, when both the package flap and the package body are comprised of the same material. Preferably, the portion of the package flap to which the tape tab is attached is corona discharge treated prior to applying the tape tab to the same to further increase the permanency of the bond between the first portion of the tape tab and the package flap. Any conventional corona discharge treatment can be used for this purpose. However, it is expressly not admitted that corona discharge treatment is known for carrying out the present invention as described above.

The tape fastening system of the present invention improves the bond security while at the same time making it more easy to remove the adhesive tape from a low caliper polyethylene film without tearing by carefully matching and optimizing the properties of the adhesive tape and the landing member (the film wrapper). These properties are optimized by matching the physical properties of the tape, its backing materials, and the film wrapper, the adhesive fastening system can give the desired refastenability without extra reinforcing materials or parts and without sacrificing bond security.

A test of how an adhesive bond behaves when it is under wrapping tension on a package containing a sanitary napkin for disposal and that best simulates a wide range of design, environmental and consumer variables is a dynamic shear test. The dynamic shear test measures the strength of an adhesive bond prior to failure in the shear mode under a force applied at a constant rate. Results of a dynamic shear test at typical conditions show a good correlation with in use performance. Thus, it has been found that the adhesive fastening system should have a Dynamic Shear Strength of greater than about 900 grams per centimeter under the test conditions hereinafter described.

In another aspect of the fastening system of the present invention, the bond security and refastenability can be enhanced by providing a landing member that has certain defined surface characteristics. The adherence surface of the landing member is textured such that it has a surface roughness having a Mean Leveling Depth of between about 2 microns and about 20 microns. These surface characteristics enhance the bond security of the adhesive fastening system.

When the fastening system is subjected to stress conditions in retaining the used sanitary napkin in the package for disposal, the tape and the landing member stretch under load. If there is too large a difference in their elongation properties, then stress is transferred to the adhesive bond which may cause peel forces which in turn cause premature failure of the adhesive bond. If the tape and the landing member have similar elongation or stretch properties, then the stress transferred to the adhesive bond is minimized and the bond tends to remain in a shear mode of failure which is stronger.

Thus, in the present invention, it has been found that the Youngs Modulus (elasticity modulus) of the landing member should be increased to more closely match the elasticity modulus of the tape (within a factor of at least about 2 or 3). Therefore, the landing member, the film wrapper, preferably has a Youngs Modulus (elasticity modulus) of greater than about 175 N/mm$^2$ in order to withstand higher stress at greater elongation.

The adhesive aggressiveness (quick-stick) to the landing member determines the bonding strength of the fastening system at light application pressures. This aggressiveness needs to be controlled so as to maximize the strength of the bond but also so as to minimize the energy transmitted to the landing member when the package is opened (especially when the tape is "jerked" off). Thus, the adhesive is preferred to have a quick-stick of at least about 35 g/cm.

The improved bond security and refastenability of the adhesive fastening system can be achieved without the need for reinforcing the landing member (which reduces the cost and improves the environmental impact of the adhesive fastening system) and with a minimum of materials (which reduce cost and improve ease of use and aesthetics.) The coating weight of the adhesive can be relatively low, preferably less than about 22 g/m$^2$. Further, the film wrapper, which does not need to be reinforced, can have a relatively low calculated caliper (nominal average thickness) of between about 0.02 mm (0.8 mil) and about 0.036 mm (1.4 mils).

BRIEF DESCRIPTION OF THE DRAWINGS

While the specification concludes with claims particularly pointing out and distinctly claiming the present invention, it is believed the invention will be better understood from the following description taken in conjunction with the accompanying drawings wherein like parts are given the same reference numeral, and:

FIG. 1 is a top plan view of a flapped sanitary napkin and one embodiment of a releasable wrapper according to the present invention;

FIG. 2 is a vertical sectional view taken along lines 2—2 of FIG. 1;

FIG. 3 is a perspective view of a wrapper and a sanitary napkin in a partially trifolded configuration;

DETAILED DESCRIPTION OF THE INVENTION

Figure 4:
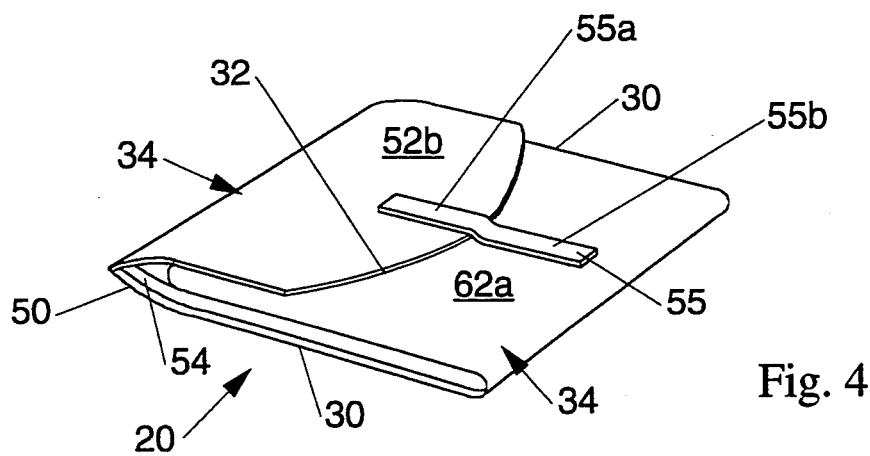
FIG. 4 is the sanitary napkin and wrapper according to FIG. 2 shown in a fully trifolded configuration.

The present invention relates to adhesive fastening systems for packages for individually packaged disposable absorbent articles like sanitary napkins and adult incontinent products. The fastening system is shown in one preferred use. It should be understood, however, that the fastening system can be used more broadly and it is not limited to use on any particular type of package.

As shown in FIG. 1, the invention is shown in conjunction with a package containing a disposable absorbent article, particularly a sanitary napkin 20. The sanitary napkin 20 is used to collect vaginal discharges, such as menses, and to prevent soiling of the wearer's clothing by such discharges. The sanitary napkin 20 has a body-facing side or face 20a and an opposed garment-facing side or face 20b. The sanitary napkin 20 features a liquid pervious topsheet 22, a liquid impervious backsheet 24, and an absorbent core 26 intermediate the topsheet 22 and the backsheet 24. The perimeter of the sanitary napkin 20 is defined by the two longitudinal side margins (or "side edges") 30 and two lateral side margins (or "end edges" or "ends") 32.

If desired, the sanitary napkin 20 may further comprise at least one flap 28 extending from a longitudinal side margin 30 of the sanitary napkin 20, and preferably two symmetrically opposite flaps 28, one extending from each longitudinal side margin 30 of the sanitary napkin 20.

The sanitary napkin 20 is superimposed on a releasable wrapper 34. The releasable wrapper 34 underlays and is releasably affixed to the outwardly oriented face of the backsheet 24 (that is, the garment-facing side 20b of the sanitary napkin 20). As used herein, "releasably affixed" refers to the condition of two or more components which may be attached and separated without destruction of or undue distortion to either component. The releasable wrapper 34 is preferably slightly larger than the sanitary napkin 20 as it is defined by its longitudinal and lateral side margins 30 and 32.

Associated with the sanitary napkin 20 and each flap 28 is a means 40 for attaching the sanitary napkin 20 to the undergarment of a wearer. Particularly, each flap 28 may have its own adhesive patch 40b associated with the face of the flap 28 which contacts the undergarment of the wearer and, the central portion of the sanitary napkin 20 laterally intermediate the flaps 28 has adhesive 40a associated with the portion of the sanitary napkin 20 which contacts the undergarment of the wearer. More preferably such adhesive fasteners 40a and 40b are both located on the outwardly oriented face of the backsheet 24.

The releasable wrapper 34 contacts the adhesive 40a of the central portion of the backsheet 24, and if desired, the adhesive 40b of the flaps 28. As used herein, "releasable" refers to the condition where a first component may be separated from a second component at least once without causing destruction or undue distortion of either component. The releasable wrapper 34 prevents contamination of such adhesive 40 prior to first use by the wearer. Also, the releasable wrapper 34 provides protection for the sanitary napkin 20 when it is inwardly trifolded and the releasable wrapper 34 is exposed.

Examining the components of the sanitary napkin 20 in more detail with continuing reference to FIG. 1, the sanitary napkin 20 has a generally centered longitudinal centerline 36. As used herein the term "longitudinal" refers to an imaginary line, axis or direction of the sanitary napkin 20, which line, axis or direction is typically centered between the side margins of the napkin and is generally aligned with the vertical plane which bisects a standing wearer into left and right body halves. The terms "lateral" or "transverse" refer to an imaginary line, axis or direction generally orthogonal the longitudinal direction and within the plane of the sanitary napkin 20, which is generally sideways aligned relative to the wearer.

The topsheet 22 is the component of the garment which is oriented towards and contacts the body of the wearer and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials and perforated polyolefinic films.

The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be sprayed with a surfactant to enhance fluid penetration to the core 26. The surfactant is typically nonionic and should be nonirritating to the skin. A surfactant density of about 0.01 milligrams per square centimeter of topsheet 22 area is suitable. A suitable surfactant is sold by the Glyco Chemical, Inc. of Greenwich, Conn. as Pegosperse 200 ML.

A particularly suitable topsheet 22 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Ethyl Corporation, Visqueen Division, of Terre Haute, Ind. has been found to work well.

The backsheet 24 may be any flexible, liquid impervious or liquid resistant material, such as a polyolefinic film, and prevents discharges collected by and contained in the sanitary napkin 20, particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. A polyethylene film, such as is sold by the Ethyl Corporation, Visqueen Division, under model XP-39385 has been found particularly well suited for this invention.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and an uniaxially elastically extensible elastomeric film such as described in the aforementioned U.S. Pat. No. 4,476,180 issued to Wnuk.

In a particularly preferred embodiment, the backsheet 24 is slightly larger than the topsheet 22 and intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the side margin of the topsheet 22. This geometry provides a marginal area of protection should the core 26 become overloaded or the sanitary napkin 20 otherwise fail. In such an embodiment the backsheet 24 and flaps 28 are preferably unitary and coextensive.

The backsheet 24 and the topsheet 22 are preferentially peripherally joined using known techniques, either entirely, so that the entire perimeter of the sanitary napkin 20 is circumscribed by such joining, or are partially peripherally joined. Any arrangement that provides for a unitary assembly and capture of the core 26 intermediate the topsheet 22 and backsheet 24 is suitable. Such an assembly has two mutually opposed major faces, one defined by the topsheet 22 and one defined by the backsheet 24.

The outwardly oriented face of the backsheet 24 preferably further comprises means 40 for attaching the sanitary napkin 20 to the undergarment of the wearer. Pressure sensitive adhesive 40a has been found to work well. Preferably a strip 40a of longitudinally oriented adhesive provides good protection against either the front or the back of the sanitary napkin 20 being detached from the wearer's undergarment. The strip 40a may be continuous or intermittent. A particularly preferred arrangement utilizes two longitudinally oriented strips 40a, one on each side of the longitudinal centerline 36.

The absorbent core 26 is the means for collecting and containing bodily discharges, particularly menses, deposited thereon or which otherwise traverse through the liquid permeable topsheet 22. The core 26 is the component of the sanitary napkin 20 which receives and retains the bodily discharges. The core 26 is conformable and nonirritating to the skin, and preferably relatively thin. The core 26 may be rectangularly or hourglass shaped. The core 26 preferably has two opposed faces, one oriented towards the backsheet 24 and one oriented towards the topsheet 22.

Suitable core 26 materials include, but are not limited to combinations of airfelt, such as cellulose wadding, and fibrated communition pulp; layers of tissue paper; and absorbent gelling materials, and any other material known in the art for this purpose.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

If it is desired to incorporate absorbent gelling materials into the core 26 of the sanitary napkin 20, absorbent gelling materials made in accordance with U.S. Pat. No. Re. 32,649 issued Apr. 19, 1988 to Brandt et al. and incorporated herein by reference for showing particularly preferred absorbent gelling materials are suitable. A suitable core 26 comprises a laminate of absorbent gelling materials and tissue may be purchased from the Grain Processing Corporation of Muscatine, Iowa under Model Number L535.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also provides for a unitary assembly.

The core 26 is preferentially joined to the topsheet 22, and may be joined to the backsheet 24. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined relationship between the first member, or component, and the second member, or component, is intended to remain for the life of the sanitary napkin 20.

Joining may be accomplished by adhesive bonding the core 26 to the topsheet 22 or the backsheet 24. The adhesive (not shown) may be applied in any suitable spray pattern, such as a spiral, or in longitudinally oriented beads. The adhesive should be surfactant resistant and of low pressure sensitivity, so as not to stick to the skin of the wearer. The components of the sanitary napkin may also be joined by fusing the components such as is described in U.S. patent application Ser. No. 07/810,774 filed in the name of Cree, et al. on Dec. 17, 1991.

The sanitary napkin 20 preferably has a caliper of less than about 4 millimeters and more preferably less than about 2 millimeters, as measured with a comparator gage having an approximately 80.0 gram test weight and an approximately 10.0 gram comparator foot having a diameter of about 2.54 centimeters and a contact surface area of approximately 5.1 square centimeters. Also, the sanitary napkin 20 should preferably have a topsheet 22 surface area of at least about 100 square centimeters to prevent discharged fluids from missing the target area.

The sanitary napkin 20 may also comprise a flap 28 extending from a longitudinal side margin 30 of the sanitary napkin 20, and preferably one flap 28 extending from each longitudinal side margin 30 of the sanitary napkin 20. The flaps 28 have a proximal end (or "proximal edge") 44 which is typically coincident with the juncture of attachment of the flap 28 to the longitudinal side margin 30 of the sanitary napkin 20. Alternatively, the proximal end 44 of the flap 28 may be joined to the sanitary napkin 20 at another location, remote from but juxtaposed with the longitudinal side margin 30.

The flaps 28 extend laterally outwardly from the sanitary napkin 20 and terminate at a distal end (or "distal edge") 46 which represents the portion of the flaps 28 furthest from the longitudinal side margins 30 of the sanitary napkin 20. The distal ends 46 of the flaps 28 are directed away from the longitudinal centerline 36 and central portion of the sanitary napkin 20. As used herein the phrase "central portion" refers to that part of the sanitary napkin 20 intermediate, particularly laterally intermediate, and defined by the proximal ends 44 of the flaps 28. The flaps 28 may be of any shape desired, with one preferred shape being shown in FIG. 1.

The flaps 28 may be comprised of an integral and contiguous extension of the topsheet 22, the backsheet 24, or a laminate of both 22 and 24. Alternatively, the flaps 28 may be made of a separate and independent piece of material joined to the longitudinal side margins 30 of the sanitary napkin 20. Each flap 28 has one face generally coextensive of the topsheet 22 and a mutually opposed face generally coextensive of the backsheet 24.

The flaps 28 preferably have a means 40 for attaching one face of the flap 28 to the wearer's undergarment or to the other flap 28. The attachment means 40 may be a mechanical fastener or, preferably, pressure sensitive adhesive 40b. If pressure sensitive adhesive 40b is selected, it should be disposed on the face of the flap 28 generally coextensive of the backsheet 24 so that when the flaps 28 are wrapped around the crotch portion of the wearer's undergarment, the adhesive 40b will face the outside of the wearer's undergarment. A generally rectangular patch of adhesive 40b on each flap 28, about 38 millimeters×19 millimeters in size, works well. Suitable pressure sensitive adhesive 40 is sold by the Anchor Continental, Inc., 3 Sigma Division of Covington, Ohio, and specified as 0.02 millimeter pass Century Adhesive A305-4.

For packaging, the flaps 28 are folded over the topsheet 22 so that the flaps 28 are in the topsheet facing relationship of FIG. 2. The flaps 28 are considered to be in a topsheet facing relationship if a line generally perpendicular the plane of the sanitary napkin 20 drawn outwardly from the topsheet 22 intercepts either face of the flap 28. The flaps 28 are preferably folded about the proximal edge 44 so that maximum coverage of the topsheet 22 is obtained. This arrangement provides a larger area of the topsheet 22 covered by the flaps 28, particularly the area of the topsheet 22 which is generally registered with the wearer's vagina, so that a sanitary and clean appearance of this portion of the topsheet 22 is promoted. It is not necessary that the flaps 28 be folded about the proximal ends 44, that the flaps 28 be in contacting relationship with the topsheet 22, or that no other folds occur between the distal and proximal ends 44 and 46 of the flaps 28. It is only necessary that the flaps 28 face towards the topsheet 22 and discourage outside contamination from readily soiling the portion of the topsheet 22 covered by the flaps 28.

Folding the flaps 28 in the configuration of FIG. 2 exposes the patch 40b of adhesive on the face of the flaps 28 generally coextensive of the backsheet 24. To prevent contamination and blocking of this adhesive patch 40b, each flap 28 may be covered with a separate and dedicated piece of release liner. In a preferred embodiment, the patches of adhesive 40b can both be covered by a single piece of release liner that forms a bridge from one flap to the other.

It will be apparent to one skilled in the art, however, that the flaps 28 may be folded over the backsheet 24 or, convolutely folded so that one flap 28 overlays the topsheet 22 and the other flap 28 overlays the backsheet 24. All such embodiments are within the spirit and scope of the claimed invention.

The releasable wrapper (or "wrapper") 34 has a perimeter defined by longitudinal edges and lateral edges. Preferably, the lateral edges of the releasable wrapper 34 extend outward beyond the respective lateral side margins 32 of the sanitary napkin 20. This arrangement provides a releasable wrapper 34 having sufficient longitudinal extent to conceal and to protect the sanitary napkin 20 in the later described folded configurations.

The wrapper 34 has opposed faces. One face is an inwardly oriented face which is oriented towards the adhesive 40 and the outwardly oriented face of the backsheet 24. The other face is an outwardly oriented face opposed to the inwardly oriented face and which is oriented away from the sanitary napkin 20.

Preferably, the inwardly oriented face is release coated, to facilitate easy and convenient manipulation of the releasable wrapper 34, and particularly separation from the adhesive 40. Silicone release coatings, as are well known in the art, have been found to work well. The releasable wrapper 34 may be zone coated with the release coating only in the areas of the adhesive 40a and 40b, or may be entirely release coated throughout the inwardly oriented face as desired.

The releasable wrapper 34 may be made of one or more sheets of material. The wrapper 34 may, for instance, comprise a two component arrangement comprising the wrapper 34 as described herein that is combined with a conventional release strip that covers the adhesive 40a attached to the inwardly oriented face of the wrapper 34. Preferably, however, the releasable wrapper 34 comprises a single sheet that both covers the adhesive 40a and serves as a package for the sanitary napkin 20.

The releasable wrapper 34 may be made of films, kraft paper, calendered paper, or other materials as are well known in the art without departure from the spirit and scope of the claimed invention. One preferred releasable wrapper 34 is made of machine glazed or machine finished paper having a basis weight of about $40.7 \times 10^{-3}$ kilograms per square meter (25 pounds per 3,000 square feet). The inwardly oriented face of the wrapper may be coated with a release coating such as silicone. Suitable release coatings are marketed by Akrosil of Menasha, Wis. as Silox 4R/O and Silox C1S. However, the releasable wrapper 34 used in the present invention preferably comprises a film.

Preferably, the releasable wrapper 34 is a flexible polyethylene film. As used herein the term "polyethylene" film refers to films which are essentially made of polyethylene, however, it is understood that polyethylene film will contain a variety of additives to provide characteristics like opacity, strength requirements, color, or any other desired characteristic that can be achieved through adding minor amounts of other substances than polyethylene into the films. The total amount of additives should be less than 45%, preferably less than 15%, by weight of film materials. Particularly for opacity of the film, titanium dioxide is commonly used in a range of 5–9%, preferably 6.8–7.8%, by weight of the film. Exemplary films for use as the releasable wrapper 34 film in the present invention are manufactured by Tredegar Industries, Inc. of Terre Haute, Ind. under the designation X-9068. The releasable wrapper 34 is preferably textured as described hereinafter to enhance the performance of the fastening system and to provide a more aesthetically pleasing appearance. The releasable wrapper may also be biodegradable such as the film disclosed in co-pending, commonly-assigned, U.S. patent application Ser. No. 07/721,066 "Disposable Absorbent Articles With Biodegradable Backsheets", Toms and Wnuk, filed on Jun. 26, 1991.

The longitudinal edge portions of the releasable wrapper 34 may be C-folded around the longitudinal side edges 30 of the sanitary napkin 20 as shown in the drawing figures, or they may extend outward to provide regions of the releasable wrapper 34 dedicated for sealing of the package as shown in U.S. Pat. No. 4,556,146 issued to Swanson. Either arrangement provides the advantage that one entire major face, particularly the face associated with the backsheet 24, is protected by the releasable wrapper 34, the longitudinal side margins 30 of the sanitary napkin 20 are likewise protected, and additionally a portion of the topsheet 22 is protected by the releasable wrapper 34.

As illustrated in FIG. 3, the sanitary napkin 20 and releasable wrapper 34 may be folded about two spaced-apart laterally oriented fold lines. As used herein, the phrase "spaced-apart laterally oriented fold lines" refers to longitudinally offset lines, generally parallel the lateral direction, and about which the sanitary napkin 20 and releasable wrapper 34 are commonly folded.

Folding the sanitary napkin 20 about the spaced-apart laterally oriented fold lines produces a folded arrangement defining three trisections, a central trisection 51 intermediate and bounded by two outboard trisections 52. The outboard trisections 52 may be more specifically described as an inner-outboard trisection 52a and an outer-outboard trisection 52b, or more simply as the first and third trisections. The central trisection 51, thus, comprises the second trisection. As used herein, inner and outer outboard trisections 52 are described relative to the central trisection 51 when the sanitary napkin 20 and releasable wrapper 34 are in the folded arrangement of FIG. 4. The inner-outboard trisection 52a is generally adjacent the central trisection 51 and intermediate such central trisection 51 and the outer-outboard trisection 52b when folded. Conversely, the outer-outboard trisection 52b is relatively further from the central trisection 51 due to the interposition of inner-outboard trisection 52a.

In the folded arrangement of FIG. 4, the package defines two mutually opposed major surfaces, one defined by the outer-outboard trisection 52b, and one defined by the central trisection 51. The arrangement of FIG. 4 produces a sanitary napkin 20 having an e-fold with a releasable wrapper 34 having a corresponding e-fold. The releasable wrapper 34 is preferably of sufficient longitudinal dimension to overlie one outboard trisection 52 and the central trisection 51. More preferably, the releasable wrapper 34 is of sufficient longitudinal dimension to overlie all three trisections 51 and 52, so that no adhesive 40a is exposed.

Referring back to FIG. 1, the releasable wrapper 34 may further comprise a means for maintaining the sanitary napkin 20 and releasable wrapper 34 in the aforementioned folded arrangement. Suitable means for maintaining the folded arrangement include hook and loop mechanical fasteners, such as are sold under the tradename Velcro; adhesive tabs, such as are illustrated in the prior art, or, possibly, adhesive 54 juxtaposed with the longitudinal edges of the releasable wrapper 34.

The drawing figures show this latter embodiment in which adhesive 54 is placed on the longitudinal edge of the releasable wrapper which overlays and faces outwardly from the topsheet 22. In one execution, the adhesive 54 may be applied to the outboard trisections 52 so that when the inner-outboard trisection 52a is folded over the central trisection 51 such trisections 50 and 52a are releasably affixed to each other and adhesive is juxtaposed with the outer-outboard trisection 52b so that it may be releasably affixed to the inner-outboard trisection 52a. Alternatively, the adhesive 54 may be applied to the central and outer-outboard trisections 50 and 52b.

Preferably in the present invention, the adhesive 54 is located on a portion of the releasable wrapper 34 that forms a package flap and is secured to another portion of the wrapper that forms the body of the package.

The adhesive 54 may be applied in a continuous strip (as shown), in an intermittent strip, or may be a single spot. It is not critical which form the adhesive 54 is applied, only that it have sufficient peel strength to maintain the folded arrangement until it is desired to conveniently open the sanitary napkin 20 and releasable wrapper 34 for the first use by the wearer and that the adhesive be refastenable to the wrapper film when the wrapper is used for disposal of a used sanitary napkin.

In a particularly preferred embodiment, the adhesive comprises and is disposed on a tab (preferably a tape tab) 55 longitudinally extending beyond the lateral edge of the outer-outboard trisection 52a. The adhesive 54 on the tape tab 55 that is not disposed longitudinally beyond such lateral edge is affixed to the exposed face of the outer-outboard trisection 52b.

The component parts of the fastening system include the tab 55, which preferably comprises a piece of tape. The tab or tape 55 comprises a first portion 55a and a second portion 55b. The first and second portions can be arranged in several different manners. For instance, they can be separate components attached to the tab 55, etc. Preferably, however, the first and second portions are contiguous segments of the tab 55.

The first portion 55a of the tape tab 55 is preferably securely attached to a first surface during manufacture of the wrapper to which the tape tab is attached. The first portion, as a result, may also be referred to as a "fixed end". In this case, the first surface 34' is a portion of wrapper 34 near the lateral (or end) edge of the third trisection 52b.

The second portion 55b of the tape 55 extends outward beyond the end of the first surface 34'. The second portion serves at least two main purposes. The second portion forms a releasable bond with the landing member 34 or second surface 34''. The second portion is also grasped by the consumer when it is desired to open and close the package. (That is, when the consumer desires to unfasten and refasten the two surfaces). The second portion, as a result, may also be referred to as a "tab portion", "user's portion", or user s end".

Optionally, the tape tab 55 can be provided with a grip tab at the distal edge of the second portion 55b of the tape tab 55. Grip tabs may be formed, for example, by folding part of the fastening surface 54 at the lateral outside end of the connective end onto itself. Grip tabs are preferably 2 mm to 8 mm, more preferably about 6 mm, wide. Grip tabs can also be provided by having the distal edge not covered by adhesive.

The tape tab 55 comprises a tape backing material which can be any of the tape backing materials well known in the art. For example, polyester films, polypropylene films, paper backings, or other materials which provide the required strength to be useful as part of a tape tab 55 to maintain the releasable wrapper package in a folded configuration before use of the sanitary napkin and to maintain the package in a folded configuration for disposal, are suitable for use as the tape backing material. Particularly, tape backing materials of polypropylene film having a caliper of about 0.15 mm have been found to perform satisfactorily.

The tape tab has a fastening surface 54 having a layer of adhesive coated onto the tape backing material. (As used herein, the term "coated" is not to be limited to any specific technique or method for applying the adhesive onto the tape backing material). The fastening system may use any suitable adhesive that provides the dynamic shear strengths, quick-stick, releasability from the landing member, and coat weight properties. The composition of the adhesive is not as important as the properties of the overall tape system as discussed hereinafter. The adhesive can, for example, be a hot melt adhesive which is coated onto the tape backing by any of the well known hot melt coating processes (e.g., by a slot coating process). Alternatively, the adhesive can be supplied in a solvent coating process. Preferably, the adhesive is an elastomeric pressure-sensitive adhesive. It is particularly preferred that such an adhesive material comprises a tackified rubber elastomer. As described hereinafter, the adhesive has preferably dynamic shear strengths, quick-stick value, and releasability in conjunction with relatively low coating weights so as to provide the enhanced performance described herein. In accordance with the present invention, it has been found that tapes (tape backing material and adhesive) such as are manufactured by the Minnesota Mining and Manufacturing Company, St. Paul, Minn., under the designation XPF-0115, have been found to provide satisfactory performance in the fastening system of the present invention.

The joining of the fixed end 55a of the tape tab 55 to the outer-outboard trisection 52b can be provided by mechanical or preferably by adhesive means. In a preferred embodiment, the tape backing of the tape tab 55 is covered across its whole width with a layer of adhesive. This adhesive, thus, not only provides the exposed fastening means at the "user's end" on the inner-outboard trisection 52a, but also the attachment to securely adhere the tape tab 55 to the outer-outboard trisection 52b at the fixed end 55a.

The adhesive tape fastening system further comprises a landing member (or "landing surface"). In a preferred embodiment of the present invention, the landing member comprises at least a portion of the unreinforced releasable wrapper 34. The adherence surface of the landing member (generally the same surface as the outer surface of the wrapper 34) is the surface onto which the adhesive of the tape tab 55 is refastenably adhered when the releasable wrapper 34 is maintained in a folded configuration to form a package around the sanitary napkin, before or after use of the sanitary napkin.

The properties of the overall fastening system, including the properties of the adhesive on the tape tab and the properties of the landing member, are important design criteria in the performance of the adhesive fastening systems of the present invention. Fastening systems for packages for individually packaged disposable absorbent articles need to provide a bond that can be opened to remove the absorbent articles for use by the wearer without destruction or damage to the landing surface, and a bond that can also be refastened at light application pressures that holds the package securely when disposing of the used absorbent article.

These values must be balanced against the environmental and economic need of reducing the materials and costs of such fastening systems. The peel strength, the dynamic shear strength of the adhesive fastening system, the quick-stick property of the adhesive, and the surface characteristics of the wrapper film have been found to be important variables in providing not only superior bond security but also refastenability without the need for additional reinforcement of the landing surface.

The peel strength of the adhesive has been found to be an important variable in determining the releasability of the adhesive fastening system. The peel strength of the adhesive measures the ease of removing the adhesive from the landing surface. The peel strength should be high enough to maintain the sanitary napkin in a folded configuration, but not so high that it exceeds the tensile strength of the landing member to ensure good refastenability. The peel strength of the adhesive of the present invention is preferably between 100 g/cm and 600 g/cm, more preferably between 100 g/cm and 400 g/cm.

The peel strength of the adhesive as defined for the present invention is measured by applying the adhesive surface of a tape tab having a width of 10 mm, to the landing surface on the wrapper film. Pressure exerted by a roller of 1,334 grams (2.5 pounds) operating at a 25.4 mm/second (1 in./second) constant speed is applied to the tape tab. The length direction of the sample is parallel to the longitudinal direction of the wrapper film. The apparatus used in evaluating the peel strength can be any tensile testing machine commercially available having a constant rate of grip separation. An EME portable tensile tester Model #570 such as distributed by EME, Inc., Newbury, Ohio has been found to be particularly useful. The initial grip distance is fixed at 50.8 mm. The speed of testing is fixed at 508 mm/minute.

The peel strength is the peak force required to remove the tape from the landing member when the tape is peeled at a 90 degree angle.

The dynamic shear strength of the adhesive fastening system has been found to be a reliable predictor of bond security in use. The object of the dynamic shear test is to measure the strength required for an adhesive bond to fail when under a given stress in the shear mode (i.e., dynamic strength). Thus, the dynamic shear strength evaluates the adhesive bond security, durability, under a constant rate of shear stress.

The dynamic shear strength test as used in the present invention is a test variation of ASTM Method A D882-83, which is incorporated herein by reference. An adhesive surface of the tape tab having a width of 10 mm is applied to the adherence surface of the landing member, the wrapper film, with a 10 mm bond length. Pressure exerted by a roller of 1,334 grams (2.5 pounds) operating at a 25.4 mm/second (1 in./second) constant speed is applied to the tape tab. The length direction of the sample is parallel to the longitudinal direction of the wrapper film. The apparatus used in evaluating the dynamic shear strength can be any tensile testing machine commercially available having a constant rate of grip separation. An EME portable tensile tester Model #570 such as distributed by EME, Inc., Newbury, Ohio has been found to be particularly useful. Light duty grips are also supplied from EME in accordance with the ASTM method. The initial grip distance is fixed at 50.8 mm. The speed of testing is fixed at 508 mm/minute. The force to induce failure of the adhesive bond (i.e., releasing of the tape from the landing member) is measured. The preferred dynamic shear strength for the adhesive fastening systems of the present invention for use on packages for sanitary napkins should be greater than about 900 g/cm, more preferably greater than about 1,000 g/cm.

The releasable wrapper 34 can be manufactured so as to provide a landing surface (or "adherence surface") that will optimize the adherence, release, and refastenability of the tape tab 55. For both strong adhesion of the adhesive to the landing member and good bond security, the landing surface must be receptive to the adhesive at low application pressures. Typically, it has been found that a "smooth" landing surface enhances bond security because the adhesive "wets" more of the surface. However, embossed landing surfaces are generally considered more aesthetically pleasing for their matte appearance at a sacrifice to bond security since the entire area is not wetted by the adhesive. It has been discovered, however, that there is an optimum surface roughness for the landing surface of the landing member, the wrapper, that provides adequate dynamic shear strength, and an aesthetically pleasing appearance.

The landing surface of the releasable wrapper 34 preferably has certain surface characteristics that are believed to enhance the bond security of the adhesive fastening system 24. Generally, the adherence surface does not exhibit a regular structure but contains a number of deviations which are divided into form, waviness and roughness. Of the various parameters of roughness, the Mean Leveling Depth, $R_{pm}$ [ISO/DIS 4287/IE or DIN 4768 test procedures], is the parameter that most strongly correlates with bond security. The Mean Leveling Depth is the mean of five leveling depths of five successive sample lengths (1/5 of the evaluation length). The leveling depth is the largest of the depths as measured from the mean line (departures from the mean line). The mean line is a line placed in the traced surface profile that is situated such that the sum of the squares of all profile deviations within the evaluation length is a minimum. For a preferred embodiment of the present invention, the Mean Leveling Depth, $R_{pm}$, is between about 2 microns and about 20 microns, more preferably between about 2 microns and about 10 microns, and most preferably between about 3 microns and about 8 microns. The surface roughness (including the Mean Leveling Depth) is measured with a Perthometer S6P profilometer apparatus such as sold by Feinpruef of Blue Ash, Ohio. The Perthometer S6P is operated with a cut-off length of 2.5 mm (evaluation length of 12.5 mm) and a T9 FocoDyn laser probe which has better accuity and does not contact the surface as do diamond stylist probes.

According to the present invention, a landing member 54, preferably being a thermoplastic film, more preferably the wrapper film 34, and having surface characteristics according to the above criteria, can have a texture, surface roughness, provided in a structured pattern or in a random pattern. In general, texturing of thermoplastic films is conducted by passing the film between a nip of a steel roll and a rubber roll. The steel roll contains the pattern such as, for example, square, round, random or other shapes as considered desirable for the particular usage of the thermoplastic film. The thermoplastic film is drawn into the nip between the two rolls which are pressed against each other. The depth of the texturing depends on the pattern provided on the steel roll. Depending on the thermoplastic film material, the steps of preheating of the thermoplastic film and cooling after the embossing can be added to the process. The landing surface of the wrapper film has generally been the surface which is embossed by the steel roll. A more detailed description of texturing processes and apparatuses can be found in U.S. Pat. Nos. 4,436,520, 4,595,021, 4,546,029, 4,376,147 or WO 88/07336. However, according to the present invention, texturing of the thermoplastic film is provided by using a process in which, for example, a patterned steel roll and a rubber roll are used in a similar way as described above. In this case, the surface of the material textured by the rubber roll is used as the adherence surface of the landing member. Preferably, the steel roll has an engraved surface. The texturing of the landing surface of the wrapper film results from the rubber roll.

The landing surface is also selected so as to have a Youngs Modulus that more nearly correlates with the elasticity modulus of the tape tab 55. The tape tab 55 will typically have a very high Youngs Modulus of between about 175 N/mm$^2$ and about 310 N/mm$^2$. Thus, the wrapper, is preferably selected so as to have a Youngs Modulus of at least about 175 N/mm$^2$, more preferably greater than about 200 N/mm$^2$, most preferably greater than about 225 N/mm$^2$ so that the Young's Modulus of the wrapper is increased to more nearly match that of the tape tab 55. The Youngs Modulus is the elasticity modulus of a material (i.e., a material constant) describing the elastic behavior of the material in issue under stress. The higher the Youngs Modulus, the less elongation that results from a given force applied to the material. In other words, a material having a higher Youngs Modulus can withstand higher stress at the same elongation than a material having a lower Youngs Modulus. While not wishing to be bound by any particular theory, it is believed that by reducing the elongation of the landing surface under stress by requiring a relatively high Youngs Modulus of greater than about 175 N/mm$^2$, a more stable adhesive interface between the adhesive and the landing surface is provided. On the other hand, it is believed that if a landing surface has a Youngs Modulus lower than about 175 N/mm$^2$, it will elongate relatively easily under stress thereby causing the adhesive interface between the tape tab and the wrapper to deform along with the elongation of the wrapper. This elongation must be compensated for by the adhesive of the tape tab along the adhesive surface. It is believed that the internal compensation of the adhesive would reduce the bond strength leading to debonding (i.e., failure of the adhesive fastening system).

The Youngs Modulus as defined for the present invention is measured in accordance with ASTM Method D 882-83 with certain modifications, that method is incorporated herein by reference. (Care should be taken to distinguish between the Youngs Modulus as defined in this test procedure versus other elasticity moduli which may have been used or measured previously and disclosed in the prior art.) The elasticity moduli previously disclosed, including patents referred to herein, are well below the required Youngs Modulus recognized by the present invention as being a lower threshold for providing the landing surface of the fastening system.) In particular, the ASTM Method A of D882-83 "Constant Rate of Grip Separation Test" to measure the elasticity modulus as defined by the ASTM method is used with only minor alterations. In the following description, particular alterations used in measuring Youngs Modulus according to the present invention are indicated. A test sample for evaluating the Youngs Modulus is 25 mm in width and 200 mm in length. The length direction of the sample is parallel to the longitudinal direction of the wrapper. Test samples are evaluated in their length direction and conditioned according to the ASTM method. The apparatus used in evaluating the Youngs Modulus can be any tensile testing machine commercially available having a constant rate of grip separation. An Instron 4201 machine such as distributed by the Instron Engineering Corporation, Canton, Mass. has been found to be particularly useful. Supply grips are also supplied from Instron in accordance with the ASTM method. The initial grip distance is fixed at 50.8 mm. The speed of testing is fixed at 508 mm/minute. Other provisions of the test procedure as well as calculation of the elastic modulus are done according to the ASTM method.

The quick-stick property of the adhesive is also important in providing for the initial bond strength and, to a lesser extent, refastenability of the fastening system. The quick-stick property of the adhesive measures the ability of the adhesive to wet the surface and form strong adhesive bonds at low application pressures. The quick-stick of the adhesive should be high enough to provide good bond security and high dynamic shear strength, but not so high that it exceeds the toughness of the landing surface to insure good refastenability. The quick-stick properties of the adhesive of the present invention is preferably greater than about 35 g/cm. The quick-stick test is performed by placing a 25.4 mm width of the tape onto the landing surface and removing the tape at a 90° angle. This test is thus a modification of PSTC No. 5 by using the landing surface as the substrate and a 17.1 g/cm$^2$ application pressure.

The improved bond security and refastenability of the adhesive fastening system can be achieved without the need for reinforcing the landing surface and with a minimum of materials. Preferred coating weights for the adhesives that provide an optimum balance between bond security and refastenability are different for each adhesive. Higher coat weights would typically provide stronger adhesive bonds at minimum application pressure while lower coat weights typically reduce the likelihood of tearing the landing surface. It has been found, however, for the adhesive fastening systems of the present invention for use on individual absorbent article packages, that the optimum coat weight of the preferred adhesive occurs preferably below about 22 g/m$^2$. More preferably, the optimum coat weight is between about 14 g/m$^2$ and about 18 g/m$^2$, most preferably between about 15 g/m$^2$ and about 16 g/m$^2$. The wrapper 34, which may, but does not need to be reinforced, can also have a relatively low calculated caliper, to reduce material costs, of between about 0.020 mm (0.8 mil) and about 0.036 mm (1.4 mils), and preferably has a caliper of about 0.025 mm (1 mil).

The ability to remove the tape tab without tearing the landing surface (i.e., refastenability) can be measured in the lab as well as in the consumers hands. In a lab test, the tape is put on as firmly as is possible and then the frequency that it tears the landing member upon being removed in a realistic way is measured. To put the tape on as firmly as possible, the tape is put on the landing surface and warmed to 37.8° C. (100° F.) for 30 minutes or more. It is then rolled on with a 2.2 kg roller and left at 37.8° C. (100° F.) for another 30 minutes. After cooling to room temperature for at least 30 minutes, the tape tab is removed by pulling rapidly as the typical consumer would. Any tearing of the landing member is considered a failure. This test provides the worst case and is about 6 times higher than the average landing member tearing experience in actual use. For the adhesive fastening systems of the present invention, the refastenability for the most severe lab test above is preferably greater than about 90%, more preferably greater than about 95%, and most preferably greater than about 98%.

The adhesive fastening system described herein could also be used on other types of packages. For instance, any of the embodiments described herein could be used on a package similar to that described in the McLaughlin patent and a sanitary napkin with a conventional release paper could be folded and inserted into such a package.

Figure 5:
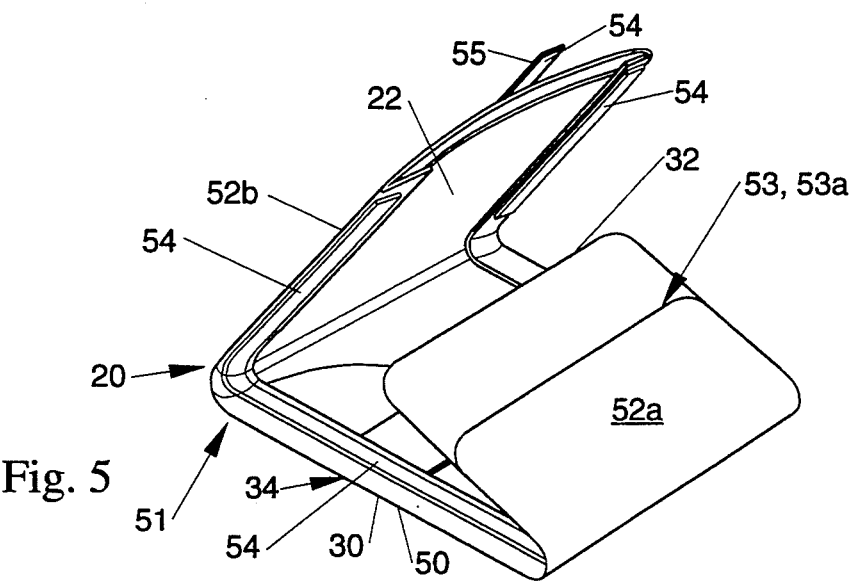
FIGS. 5-7 are perspective views of the sanitary napkin similar to FIG. 3 which show possible locations for a flap feature on the releasable wrapper.
Figure 6:
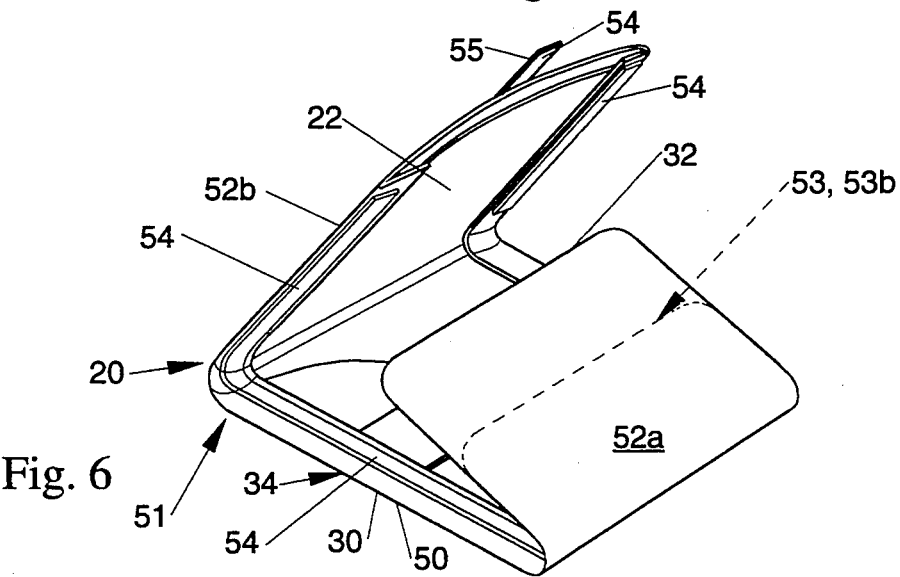
Figure 7:
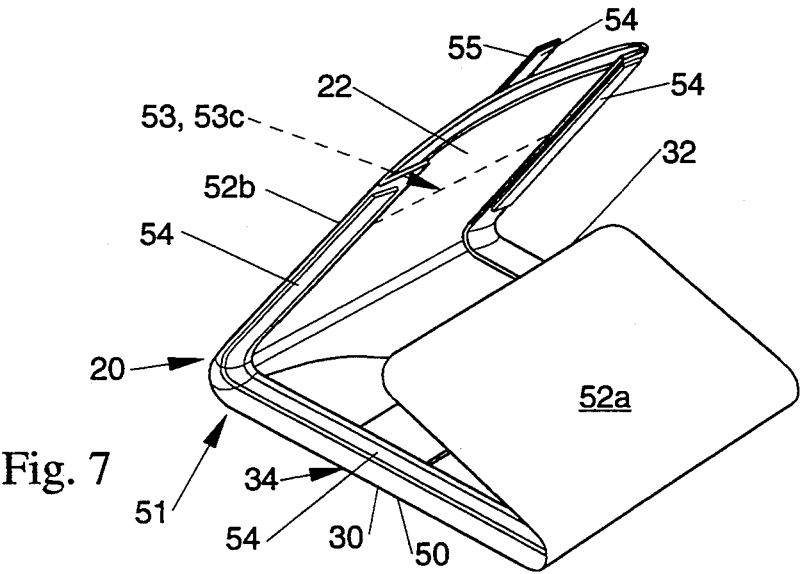

The releasable wrapper 34 (as shown in FIGS. 5-7) may also comprise a second flap (or "disposal flap", "disposal pouch", or "pouch") 53 to assist in the disposal of the sanitary napkin 20. (The first flap is the package flap described above formed by the outer-outboard trisection 52b which is used to close the individual package.) A suitable disposal flap (or pouch) is described in U.S. Pat. No. 4,556,146 issued to Swanson, et al., the disclosure of which is hereby incorporated by reference herein.

The disposal flap 53 can be used with releasable wrapper 34 embodiments that are configured to wrap the longitudinal side margins of the sanitary napkin in a C-fold (such as those shown in the drawings). In other embodiments, the flap 53 can be used with releasable wrappers 34 that are configured to overlay only one major surface of the sanitary napkin 20 (i.e., not configured to wrap the longitudinal side margins of the sanitary napkin). In still other alternative embodiments, the flap (and/or any other feature described in the Swanson, et al. patent or described herein) could be used with releasable wrappers 34 that are not configured to wrap the longitudinal side margins of the sanitary napkin, and/or are also only folded about a single transverse axis.

There are numerous possible locations on the releasable wrapper 34 for such a disposal flap 53. The disposal flap 53 can be located on either face of the wrapper, the inwardly oriented face of the wrapper 34, or the outwardly oriented face. The disposal flap 53 is typically located at one of the ends of the wrapper 34. The disposal flap 53 could, thus, be located on one or more of these faces at the end of the inner-outboard trisection 52a, or at the end of the outer-outboard trisection 52b.

FIGS. 5-7 show three preferred locations for the disposal flap 53. These are designated 53a, 53b, and 53c respectively. The disposal flap in FIG. 5 designated 53a is located at the end of the inner outboard trisection 52a. The disposal flap 53a is located on the outwardly oriented face of the wrapper 34. The disposal flap in FIG. 6 designated 53b is located on the inwardly oriented face of the same trisection. The disposal flap in FIG. 7 designated 53c is located on the inwardly oriented face of the outer outboard trisection 52b. The position of the disposal flap 53 may be chosen (as described below) to provide more options for wrapping the used sanitary napkin for disposal.

The sanitary napkin 20 can be configured for disposal in at least three different ways. The user can roll up the used sanitary napkin 20, and insert it in the disposal pouch (that is, under the disposal flap 53). The remainder of the releasable wrapper 34 can then be folded, rolled, wrapped, etc. around the portion of the disposal pouch 53 containing the sanitary napkin 20. If the releasable wrapper 34 is provided with a tape tab 55, in such a case, the tape tab 55 can be used to secure the releasable wrapper in a folded or rolled up configuration. Alternatively, the sanitary napkin can be folded or rolled up and placed on the end of the releasable wrapper 34 opposite the end containing the disposal flap. The sanitary napkin can then be rolled up in the wrapper 34. The disposal flap 53 can then be pulled over the rolled up portion of the releasable wrapper 34 to secure the package in a rolled up configuration. Alternatively, if in the previous alternative the flap 53 is on the opposite side of the releasable wrapper that the sanitary napkin is placed on and rolled up in, the disposal flap 53 can be turned inside out and pulled over the rolled up sanitary napkin 20 to secure the package.

The alternative location for the disposal flap designated 53b is an especially preferred embodiment because it allows the sanitary napkin 20 to be configured for disposal in all three alternative ways. The other two alternative locations for the disposal flap 53 are not as suitable if the user chooses the alternative of placing the sanitary napkin under the diposal flap 53 and desires to roll up the sanitary napkin 20 and fasten the rolled up sanitary napkin in a rolled up configuration with the adhesive tab 55.

It will be apparent to one skilled in the art that other variations are feasible and within the spirit and scope of the claimed invention. For example, combinations of the foregoing embodiments are feasible, and other means for maintaining the sanitary napkin 20 within the folded arrangement may be utilized. Additionally, other asymmetric arrangements may be utilized and adjustments in the relative sizes of the sanitary napkin 20 and releasable wrapper 34 may be made to accommodate the desired package size. All such variations are within the scope of the claimed invention.

While a preferred sanitary napkin embodiment of the present invention has been described, numerous other sanitary napkin embodiments could be provided with the fastening system and wrapper of the present invention. Some such sanitary napkins are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al., U.S. Pat. Nos. 5,009,653 and 4,950,264, issued to Osborn on Apr. 23, 1991 and Aug. 21, 1990, respectively, U.S. Pat. No. 4,917,697 entitled "Sanitary Napkin Having Flaps and Stress Relief Means" which issued to Osborn, III, et al. on Apr. 17, 1990, U.S. Pat. No. 4,687,478, entitled "Shaped Sanitary Napkin With Flaps", which issued to Van Tilburg on Aug. 18, 1987, U.S. Pat. No. 4,589,876, entitled "Sanitary Napkin", which issued to Van Tilburg on May 20, 1986, and U.S. Pat. No. 4,285,343, entitled "Sanitary Napkin", which issued to McNair on Aug. 25, 1981.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An individually packaged absorbent article comprising:

an absorbent article having a body-facing side, a garment-facing side, two longitudinal and two lateral side margins;

a package containing said absorbent article, said package having a package body and a package flap; and an adhesive tape fastening system for fastening said package flap to said package body, said tape fastening system comprising:

a) a tape tab comprising a first portion affixed to said package flap, and a second portion for releasably fastening said flap to said package body, said second portion comprising a fastening surface having an adhesive thereon; and b) a portion of said package body comprising a landing surface to which said fastening surface of said tape is adhered, said portion of said package body comprising a film having a nominal average caliper of between about 0.020 mm and about 0.036 mm, and wherein said tape fastening system has a Dynamic Shear Strength of greater than about 900 grams force per centimeter when a 10 mm wide sample of said tape tab is applied to said landing surface and said sample and landing surface are pulled in opposite directions at a rate of 508 mm/minute.

2. The absorbent article of claim 1 wherein said landing surface has a surface roughness with a Mean Leveling Depth of between about 2 microns and about 10 microns.

3. The absorbent article of claim 1 wherein said landing surface has a Young's Modulus of greater than about 175 N/mm$^2$.

4. The absorbent article of claim 1 wherein said adhesive has a quick stick of greater than about 35 g/cm.

5. The absorbent article of claim 1 wherein said adhesive has a coat weight of less than about 22 g/m$^2$.

6. An individually packaged absorbent article comprising:

an absorbent article having a body-facing side; a garment-facing side, two longitudinal and two lateral side margins;

a package containing said absorbent article, said package having package body and a package flap; and an adhesive tape fastening system for fastening said package flap to said package body, said tape fastening system comprising:

a) a tape tab comprising a first portion affixed to said package flap, and a second portion for releasably fastening said flap to said package body, said second portion comprising a fastening surface having an adhesive thereon, wherein the coat weight of said adhesive is between about 14 g/m$^2$ and about 18 g/m$^2$; and b) a portion of said package body comprising a landing surface to which said fastening surface of said tape is adhered, said portion of said package body comprising a film having a nominal average caliper of between about 0.020 mm and about 0.036 mm, a Youngs Modulus of greater than about 200 N/mm$^2$, a surface roughness with a Mean Leveling Depth of between about 3 microns and about 8 microns; and wherein said fastening system has a quick stick value of more than about 35 g/cm.

7. The absorbent article of claim 6 wherein fastening system has a Dynamic Shear Strength of greater than about 900 grams force/centimeter when a 10 mm wide sample of said tape tab is applied to said landing surface and said sample and landing surface are pulled in opposite directions at a rate of 508 mm/minute.

8. The absorbent article of claim 6 wherein the absorbent article is an adult incontinent brief.

9. The absorbent article of claim 6 wherein the absorbent article is a sanitary napkin.

10. The absorbent article of claim 6 wherein said first portion of said tape tab is affixed to a portion of said package flap, and at least said portion of said package flap has been corona discharge treated.

* * * * *